United States Patent [19]

Okawa et al.

[11] Patent Number: 5,565,540
[45] Date of Patent: Oct. 15, 1996

[54] METHOD FOR THE PREPARATION OF SIOH-CONTAINING ORGANOSILOXANE OLIGOMER

[75] Inventors: Tadashi Okawa; Shuji Yamada, both of Chiba Prefecture, Japan

[73] Assignee: Dow Corning Toray Silicon Co., Ltd., Tokyo, Japan

[21] Appl. No.: 95,330

[22] Filed: Jul. 21, 1993

[30] Foreign Application Priority Data

Jul. 29, 1992 [JP] Japan ................................. 4-222176

[51] Int. Cl.$^6$ ............................................... C08G 77/08
[52] U.S. Cl. .................. 528/14; 528/21; 556/453; 556/456
[58] Field of Search ................ 528/14, 21; 556/453; 553/456

[56] References Cited

U.S. PATENT DOCUMENTS

| | | | |
|---|---|---|---|
| 3,489,782 | 1/1970 | Pruvost et al. | 556/453 |
| 3,759,867 | 9/1973 | Merrill et al. | 528/14 |
| 4,387,196 | 6/1983 | Bonnet et al. | 528/14 |
| 4,465,849 | 8/1984 | Terae et al. | 556/453 |
| 4,536,590 | 8/1985 | Brown, Jr. | 556/453 |
| 4,855,472 | 8/1989 | Burkhardt | 556/453 |
| 5,130,399 | 7/1992 | Ikeno et al. | 528/14 |
| 5,300,607 | 4/1994 | Nakanishi et al. | 528/14 |

FOREIGN PATENT DOCUMENTS

| | | | |
|---|---|---|---|
| 0652523 | 11/1962 | Canada | 528/14 |
| 0683141 | 3/1964 | Canada | 528/14 |
| 0693327 | 8/1964 | Canada | 528/14 |
| 0544257A2 | 11/1992 | European Pat. Off. . | |
| 50-111198 | 9/1975 | Japan . | |
| 61-108628 | 5/1986 | Japan | 528/21 |
| 63-312325 | 12/1988 | Japan | 528/21 |

*Primary Examiner*—Robert E. Sellers
*Attorney, Agent, or Firm*—Sharon K. Severance

[57] ABSTRACT

The present invention pertains to a method for the preparation of organosiloxane oligomer with the general formula $$R^1{}_3SiO(R^2{}_2SiO)_nH$$

where each $R^1$ and $R^2$ are independently monovalent hydrocarbon groups and n has a value of 1 to 10; wherein the method comprises cohydrolyzing a triorganohalosilane and diorganodihalosilane in the presence of a basic compound in a two-layer liquid system comprised of an aqueous layer and an organic solvent layer. The method of the instant invention is a high-yield method for the preparation of organosiloxane oligomer having the silicon-bonded hydroxyl group at only one molecular chain terminal.

14 Claims, No Drawings

METHOD FOR THE PREPARATION OF SIOH-CONTAINING ORGANOSILOXANE OLIGOMER

BACKGROUND OF THE INVENTION

SiOH-containing organosilicon compounds are excellent plasticizers for silicone rubbers. Organosilicon compounds of this type are exemplified by diorganosilanediols such as diphenylsilanediol, etc., and by organosiloxane oligomers such as trimethylsiloxydiphenylsilanol, alpha,omega-dihydroxymethylphenylsiloxane oligomer, alpha,omega-dihydroxydiphenylsiloxane oligomer, and others.

In Japanese Patent Application Number Hei 3-336078 [336,078/1991] the present inventors have already proposed a method for the preparation of triorganosiloxydiphenylsilanol. The method for the preparation of triorganosiloxydiphenylsilanol proposed in Japanese Patent Application Number Hei 3-336078 characteristically consists of the following: a first step in which triorganochlorosilane is very carefully hydrolyzed to give triorganosilanol; a second step in which a reaction mixture is prepared by a dehydrochlorination reaction between the triorganosilanol and a diphenyldihalosilane; a third step in which triorganosiloxydiphenylhalosilane is purified from the resulting reaction mixture; and a fourth step in which the triorganosiloxydiphenylhalosilane is very carefully hydrolyzed. However, the method proposed in Japanese Patent Application Number Hei 3-336078 suffers from a complicated, four-step reaction scheme and from a low overall yield of the triorganosiloxydiphenylsilanol.

It is an object of the present invention the introduction of a high-yield method for the preparation of single-terminal SiOH-endblocked organosiloxane oligomer.

SUMMARY OF THE INVENTION

The present invention relates to a method for the preparation of organosiloxane oligomer. More specifically, the present invention relates to a high-yield method for the preparation of organosiloxane oligomer that carries the siliconbonded hydroxyl group at one and only one molecular chain terminal (hereinafter referred to as single-terminal SiOH-endblocked organosiloxane oligomer).

THE INVENTION

The present invention relates to a method for the preparation of organosiloxane oligomer with the general formula $$R^1_3SiO(R^2_2SiO)_nH$$

where each $R^1$ and $R^2$ are independently monovalent hydrocarbon groups and n has a value of 1 to 10; wherein the method comprises cohydrolyzing triorganohalosilane and diorganodihalosilane in the presence of a basic compound in a two-layer liquid system comprised of an aqueous layer and an organic solvent layer.

The triorganohalosilane used in the method of the present invention has the following general formula:

$$R^1_3SiX$$

Each $R^1$ in the preceding formula is independently a monovalent hydrocarbon group. $R^1$ may be exemplified by, but not limited to, alkyl groups such as methyl, ethyl, propyl, butyl, pentyl, and others; alkenyl groups such as vinyl, allyl, butenyl, pentenyl, hexenyl, and others; aryl groups such as phenyl, tolyl, xylyl, and others; aralkyl groups such as benzyl, phenethyl, and others; and substituted alkyl groups such as chloromethyl, 3,3,3-trifluoropropyl, and others. X in the preceding formula is a halogen atom. X may be exemplified by the chlorine atom and bromine atom with the chlorine atom being preferred. The triorganohalosilane under consideration may be exemplified by, but not limited to, trimethylchlorosilane, trimethylbromosilane, triethylchlorosilane, dimethylethylchlorosilane, dimethylvinylchlorosilane, dimethylphenylchlorosilane, methyldiphenylchlorosilane, diphenylvinylchlorosilane, and others. Trimethylchlorosilane, dimethylvinylchlorosilane, and dimethylphenylchlorosilane are specifically preferred as the triorganohalosilane.

The diorganodihalosilane used by the present invention has the following general formula:

$$R^2_2SiX_2$$

Each $R^2$ in the preceding formula is independently a monovalent hydrocarbon group. $R^2$ may be exemplified by, but not limited to alkyl groups such as methyl, ethyl, propyl, butyl, pentyl, and others; alkenyl groups such as vinyl, allyl, butenyl, pentenyl, hexenyl, and others; aryl groups such as phenyl, tolyl, xylyl, and others; aralkyl groups such as benzyl, phenethyl, and others; and substituted alkyl groups such as chloromethyl, 3,3,3-trifluoropropyl, and others. The organosiloxane oligomer afforded by the method of the present invention is particularly well qualified for application as a silicone rubber plasticizer when at least one of these groups $R^2$ is phenyl. X in the preceding formula is a halogen atom. X may be exemplified by the chlorine atom and bromine atom with the chlorine atom being preferred. This diorganodihalosilane may be exemplified by, but not limited to dimethyldichlorosilane, dimethyldibromosilane, methylethyldichlorosilane, methylvinyldichlorosilane, methylphenyldichlorosilane, diphenyldichlorosilane, phenylvinyldichlorosilane, and others. Methylphenyldichlorosilane and diphenyldichlorosilane are specifically preferred as the diorganodihalosilane.

While no specific restriction attaches to the mixing amounts for the triorganohalosilane and diorganodihalosilane in the method of the present invention, values of at least 1 are preferred for the ratio (moles of triorganohalosilane)/(moles of diorganodihalosilane) and values in the range of 3 to 5 are specifically preferred for this ratio. When the value of (moles of triorganohalosilane)/(moles of diorganodihalosilane) falls below 1, the resulting organosiloxane oligomer has a reduced compatibility with silicone rubber and will separate out from silicone rubber. Moreover, the yield of organosiloxane oligomer product based on starting diorganodihalosilane becomes constant at values for this ratio in excess of 5, and the starting triorganohalosilane simply becomes an excess.

The method of the present invention comprises the cohydrolysis of the above-described triorganohalosilane and diorganodihalosilane in the presence of a basic compound in a two-layer liquid system composed of an aqueous layer and an organic solvent layer. The basic compound used by the present invention captures and binds the hydrogen halide produced by halosilane hydrolysis and thereby also advantageously functions to suppress cleavage of the siliconphenyl bond by the evolved hydrogen halide. The basic compound may be exemplified by, but not limited to, inorganic basic compounds such as sodium hydroxide, potassium hydroxide, calcium hydroxide, sodium carbonate, potassium carbonate, calcium carbonate, sodium bicarbonate, potassium bicarbonate, ammonia, and others, and by organic basic compounds such as trimethylamine, tributylamine, ethylenediamine, pyridine, and others. In order to fulfill the purpose given above, the basic compound is preferably added at from equivalency to a 20 mol% excess referred to the number of moles of hydrogen halide produced. and more preferably at from equivalency to a 10 mol% excess referred to the number of moles of hydrogen halide produced.

With regard to the organic solvent used in the method of the present invention to form the two layers (aqueous layer and organic solvent layer), no specific restriction attaches to this organic solvent as long as it is not compatible with water in any proportion. Nonpolar organic solvents are preferred. Such organic solvents may be exemplified by, but not limited to, aliphatic solvents such as pentane, hexane, heptane, octane, nonane, decane, undecane, and others; cyclic aliphatic solvents such as cyclohexane, cycloheptane, cyclooctane, and others; aromatic solvents such as toluene, xylene, and others; and mineral spirit. Aromatic solvents such as toluene, xylene, and others are particularly preferred. The mixing quantities of water and organic solvent are again not specifically restricted, but quantities are preferably used that yield a concentration of 20 to 70 weight % for the organosiloxane oligomer product. The productivity in the process of separating the organosiloxane oligomer from the organic solvent layer becomes poor when the organosiloxane oligomer concentration drops below 20 weight %. The organosiloxane oligomer is insufficiently soluble at concentrations in excess of 70 weight %.

The temperature in the reaction system is not specifically restricted in the method of the present invention, but temperatures of 10° C. to 100° C. are preferred and temperatures of 30° C. to 90° C. are more preferred. The cohydrolysis rate is slow at reaction system temperatures below 10° C., while secondary reactions predominate at temperatures in excess of 100° C. The temperature in the reaction system can be controlled by cooling the reactor with cooling water, etc., and by adjusting the rate of halosilane addition.

Any excess addition of the basic compound is preferably neutralized in the method of the present invention. Said neutralization of the basic compound is effected by the addition of a weakly acidic compound such as acetic acid, carbonic acid, propionic acid, and others. In the absence of neutralization of the basic compound, the basic material can also be removed by thoroughly washing the organic solvent layer with water. Subsequent distillation of the organic solvent from the organic solvent layer affords organosiloxane oligomer made up mainly of single-terminal SiOH-endblocked organosiloxane oligomer.

The organosiloxane oligomer produced by the method of the present invention consists mainly of organosiloxane oligomer with the following general formula.

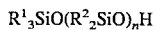

$R^1_3SiO(R^2_2SiO)_nH$ where each $R^1$ and $R^2$ are independently monovalent hydrocarbon groups. $R^1$ and $R^2$ may be exemplified by, but not limited to, alkyl groups such as methyl, ethyl, propyl, butyl, pentyl, and others; alkenyl groups such as vinyl, allyl, butenyl, pentenyl, hexenyl, and others; aryl groups such as phenyl, tolyl, xylyl, and others; aralkyl groups such as benzyl, phenethyl, and others; and substituted alkyl groups such as chloromethyl, 3,3,3-trifluoropropyl, and others. The organosiloxane oligomer afforded by the method of the present invention is particularly suited to application as a silicone rubber plasticizer when at least one of the groups $R^2$ is phenyl. In addition, n in the preceding formula is a number with a value of 1 to 10 and preferably with a value of 1 to 5. The triorganosilanol (n=0) does not perform satisfactorily as a plasticizer for silicone rubber. On the other hand, a reduced miscibility with silicone rubber occurs in the case of organosiloxane oligomer with n>10 up to the level of the organopolysiloxane, and a satisfactory performance as a plasticizer for silicone rubber is again absent. One advantage of the method of the present invention is that it selectively produces organosiloxane oligomer in which n in the preceding formula is 1 to 10. The organosiloxane oligomer produced by the method of the present invention will contain some SiOH-free organosiloxane oligomer as by-product, but the removal of this by-product in a separate purification process is optional. Because the organosiloxane oligomer produced by the method of the present invention consists mainly of the single-terminal SiOH-endblocked organosiloxane oligomer, it can be used as a plasticizer for silicone rubbers, as a blowing agent for RTV rubber foams, and others.

So that those skilled in the art can understand and appreciate the invention taught herein, the following examples are presented, being it understood that these examples should not be used to limit the scope of this invention found in the claims attached hereto.

The physical properties of the silicone rubbers were measured by the methods stipulated in JIS K-6301. The storage stability was measured as follows: the silicone rubber base was held for 4 weeks at room temperature, and the roll workability was then evaluated during conversion of the stored silicone rubber base into the silicone rubber composition. The appearance was evaluated by holding the cured silicone rubber at room temperature and visually inspecting its surface.

EXAMPLE 1

1,250 mL water and 1,250 mL toluene were introduced into a four-neck flask equipped with a reflux condenser, stirrer, addition funnel, and thermometer. 425 g sodium hydroxide was introduced into the stirred system and dissolved. The liquid temperature was then adjusted to 25° C. and a mixture of 670 g (6.2 mol) trimethylchlorosilane and 520.8 g (2.1 mol) diphenyldichlorosilane was gradually dripped into the system from the addition funnel. The addition rate was adjusted in order to complete addition in 3 hours, and the liquid temperature during this interval was maintained at 25° C. to 30° C. After then stirring for 30 minutes, 15 g acetic acid was added to the system in order to neutralize the excess sodium hydroxide and yield a weakly acidic aqueous layer. The aqueous layer was subsequently discharged from the four-neck flask and the toluene layer was washed twice with water. The toluene and low boilers were distilled off by heating the toluene layer at reduced pressure to yield 527.2 g of a microturbid, colorless, and transparent liquid.

Analysis of this microturbid, colorless, and transparent liquid by $^1H$ nuclear magnetic resonance spectroscopy gave the following results: content of silicon-bonded hydroxyl groups=4.4 weight %, diphenylsiloxane unit: trimethylsiloxane unit molar ratio=59:41. Analysis of this material by gas chromatography confirmed it to be a mixture of organosiloxane oligomers with the following formulas.

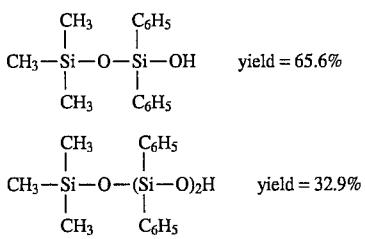

other component:

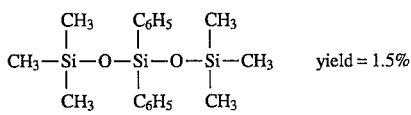

EXAMPLE 2

100 mL water and 100 mL toluene were introduced into a four-neck flask equipped with a reflux condenser, stirrer, addition funnel, and thermometer. 26.2 g (635.2 mmol) sodium hydroxide was introduced into the stirred system and dissolved. The liquid temperature was then adjusted to 25° C. and a mixture of 33.2 g (305.8 mmol) trimethylchlorosilane and 41.7 g (164.7 mmol) diphenyldichlorosilane was gradually dripped into the system from the addition funnel. The addition rate was adjusted in order to complete addition in 1 hour, and the liquid temperature during this interval was maintained at 25° C. to 30° C. After then stirring for 30 minutes, 3 g acetic acid was added to the system in order to neutralize the excess sodium hydroxide and yield a weakly acidic aqueous layer. The aqueous layer was subsequently discharged from the four-neck flask and the toluene layer was washed twice with water. The toluene and low boilers were distilled off by heating the toluene layer at reduced pressure to yield 37.9 g of a microturbid, colorless, and transparent liquid.

Analysis of this microturbid, colorless, and transparent liquid by $^1$H nuclear magnetic resonance spectroscopy gave the following results: content of silicon-bonded hydroxyl groups=4.0 weight %, diphenylsiloxane unit: trimethylsiloxane unit molar ratio=71:29. Analysis of this material by gas chromatography confirmed it to be a mixture of organosiloxane oligomers with the following formulas

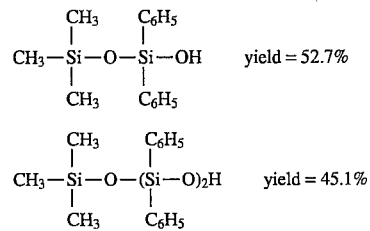

other component:

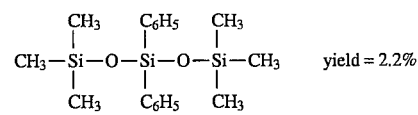

COMPARISON EXAMPLE 1

164.8 g (651.2 mmol) diphenyldichlorosilane and 300 mL tetrahydrofuran were introduced into a four-neck flask equipped with reflux condenser, stirrer, addition funnel, and thermometer. The mixture of 60 g (542 7 mmol 81.4% purity) trimethylsilanol and 65.9 g (651.2 mmol) triethylamine was then dripped in while stirring at room temperature. The reaction was stirred for an additional 1 hour at room temperature after the completion of addition, the salt by-product was filtered off, and the filtrate was distilled in vacuum to yield 118.7 g of a fraction at 136.5° C. to 142° C./2 mmHg. This fraction was confirmed to consist of trimethylsiloxydiphenylchlorosilane from the results of analysis by gel permeation chromatography, nuclear magnetic resonance spectroscopy, and infrared spectroscopy.

24.0 g (285.5 mmol) sodium bicarbonate and 250 mL water were placed in a four-neck flask equipped with reflux condenser, stirrer, addition funnel, and thermometer, and a hexane (200 mL) solution of 70 g of the trimethylsiloxydiphenylchlorosilane prepared as described above was dripped in at room temperature while stirring. Stirring was continued for another 8 hours at 50° C. after the completion of addition. A small quantity of a crystalline solid by-product was filtered off and the hexane was separated from the filtrate. This was washed with water, dried, and the solvent was then distilled off by heating in vacuo to afford 58.7 g of a colorless, transparent liquid, Analysis of this colorless, transparent liquid by gel permeation chromatography, nuclear magnetic resonance spectroscopy, and infrared spectroscopy confirmed it to be trimethylsiloxydiphenylsilanol (purity 96.9%). The overall yield of trimethylsiloxydiphenylsilanol was 61.7%.

APPLICATION EXAMPLE 1

100 weight parts organopolysiloxane with average degree of polymerization=3,000 (99.82 mol % dimethylsiloxane units, 0.18 mol % methylvinylsiloxane units), 32 weight parts dry-method silica with specific surface=300 m$^2$/g, and 8.0 weight parts of the organosiloxane oligomer prepared in Example 1 were first blended, then mixed in a kneader mixer, and finally heat-treated for 2 hours at 170° C. to yield a silicone rubber base. A silicone rubber composition was prepared by the addition of 0.4 weight parts 2,5-dimethyl-2,5-di(tert-butylperoxy)hexane to 100 weight parts of the silicone rubber base with mixing to homogeneity on a two-roll mill. The roll workability at this point was excellent. This composition was then press-molded for 10 minutes at 170° C./20 kg/cm$^2$ to yield silicone rubber with a thickness of 2 mm. This silicone rubber was held for 4 hours in a hot-air circulation oven maintained at 200° C. Table 1 reports the physical properties of the silicone rubber obtained as a result,

APPLICATION EXAMPLE 2

For the purposes of comparison, a silicone rubber composition was fabricated as above, but in this case adding diphenylsilanediol in place of the Example 1 organosiloxane oligomer that was used in Application Example 1. Silicone rubber was prepared by curing this composition as in Application Example 1, and the physical properties of this silicone rubber are also reported in Table 1.

TABLE 1

|  | Application Example 1 | Application Example 2 |
|---|---|---|
| Hardness (JIS A) | 32 | 35 |
| tensile strength (kgf/cm$^2$) | 72 | 53 |
| tear strength (kgf/cm) | 25 | 17 |
| elongation (%) | 670 | 890 |
| storage stability | excellent | excellent |
| appearance of the silicone rubber | excellent | white spots appeared |

APPLICATION EXAMPLE 3

100 weight parts organopolysiloxane with average degree of polymerization=3,000 (99.82 mol % dimethylsiloxane units, 0.1 mol % methylvinylsiloxane units), 32 weight parts dry-method silica with specific surface=300 m$^2$/g, and 8.0 weight parts of the organosiloxane oligomer prepared in Example 2 were first blended, then mixed in a kneader mixer, and finally heat-treated for 2 hours at 170° C. to yield a silicone rubber base. To 100 weight parts of this silicone rubber base were added 0.5 weight parts dimethylsiloxane-methylhydrogensiloxane copolymer (viscosity at 25° C.=5 centistokes, silicon-bonded hydrogen content=0.8 weight %), 0.06 weight parts monomethyltris(monomethylbutynoxy)silane, and sufficient chloroplatinic acid/tetramethyldivinyldisiloxane complex to provide 15 ppm platinum metal in the silicone rubber composition. This was mixed to homogeneity on a two-roll mill to give a silicone rubber composition. This silicone rubber composition was press-molded for 5 minutes at 150° C./20 kgf/cm$^2$ to give silicone rubber with a thickness of 2 mm. The physical properties of this silicone rubber are reported in Table 2.

APPLICATION EXAMPLE 4

For the purposes of comparison, a silicone rubber composition was fabricated as above, but in this case adding diphenylsilanediol in place of the Example 2 organosiloxane oligomer that was used in Application Example 3. Silicone rubber was prepared by curing this composition as in Application Example 3, and the physical properties of this silicone rubber are also reported in Table 2.

TABLE 2

|  | Application Example 3 | Application Example 4 |
|---|---|---|
| Hardness (JIS A) | 28 | 28 |
| tensile strength (kgf/cm$^2$) | 67 | 50 |
| tear strength (kgf/cm) | 23 | 14 |
| elongation (%) | 650 | 910 |
| storage stability | excellent | excellent |
| appearance of the silicone rubber | excellent | white dots appeared |

The method of the present invention for the preparation of organosiloxane oligomer is characterized by its ability to afford single-terminal SiOH-endblocked organosiloxane oligomer in high yields.

What is claimed is:

1. A method for the preparation of organosiloxane oligomers with the general formula $$R^1{}_3SiO(R^2{}_2SiO)_nH$$

where each $R^1$ and $R^2$ are independently monovalent hydrocarbon groups and n has a value of 1 to 10; wherein the method comprises cohydrolyzing a triorganohalosilane and diorganodihalosilane in the presence of a basic compound in a two-layer liquid system consisting of an aqueous layer and a nonpolar organic solvent layer wherein the triorganohalosilane and diorganodihalosilane are present in a ratio of at least 1 mole triorganohalosilane to 1 mole diorganodihalosilane.

2. A method as claimed in claim 1 wherein the triorganohalosilane is selected from triorganohalosilanes having the formula $$R^1{}_3SiX$$

where each $R^1$ is independently a monovalent hydrocarbon group and X is a halogen atom.

3. A method as claimed in claim 2 wherein the triorganohalosilane is trimethylchlorosilane.

4. A method as claimed in claim 2 wherein the triorganohalosilane is dimethylvinylchlorosilane.

5. A method as claimed in claim 2 wherein the triorganohalosilane is dimethylphenylchlorosilane.

6. A method as claimed in claim 1 wherein the diorganodihalosilane is selected from diorganodihalosilanes having the formula $$R^2{}_2SiX_2$$

where each $R^2$ is independently a monovalent hydrocarbon group and X is a halogen atom.

7. A method as claimed in claim 6 wherein the diorganodihalosilane is methylphenyldichlorosilane.

8. A method as claimed in claim 6 wherein the diorganodihalosilane is diphenyldichlorosilane.

9. A method as claimed in claim 1 wherein the basic compound is selected from the group consisting sodium hydroxide, potassium hydroxide, calcium hydroxide, sodium carbonate, potassium carbonate, calcium carbonate, sodium bicarbonate, potassium bicarbonate, ammonia, trimethylamine, tributylamine, ethylenediamine, and pyridine.

10. A method as claimed in claim 1 wherein the nonpolar organic solvent is selected from the group consisting of aliphatic solvents, cyclic aliphatic solvents; aromatic solvents; and mineral spirit.

11. A method as claimed in claim 1 wherein the organic solvent is toluene.

12. A method as claimed in claim 1 wherein the organic solvent is xylene.

13. A method as claimed in claim 1 wherein the ratio of moles of triorganohalosilane to moles of diorganodihalosilane has a value of 3 to 5.

14. A method as claimed in claim 1 wherein the cohydrolysis is conducted at temperature of 10° C. to 100° C.

* * * * *